(12) United States Patent
Sasaki

(10) Patent No.: US 10,321,802 B2
(45) Date of Patent: Jun. 18, 2019

(54) ENDOSCOPE APPARATUS AND METHOD FOR OPERATING ENDOSCOPE APPARATUS

(71) Applicant: OLYMPUS CORPORATION, Tokyo (JP)

(72) Inventor: Hiroshi Sasaki, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 155 days.

(21) Appl. No.: 15/213,702

(22) Filed: Jul. 19, 2016

(65) Prior Publication Data

US 2016/0324398 A1    Nov. 10, 2016

Related U.S. Application Data

(63) Continuation of application No. PCT/JP2015/051305, filed on Jan. 20, 2015.

(30) Foreign Application Priority Data

Jan. 22, 2014    (JP) ................................. 2014-009202

(51) Int. Cl.
*A61B 1/00*    (2006.01)
*A61B 1/12*    (2006.01)
(Continued)

(52) U.S. Cl.
CPC ...... *A61B 1/00009* (2013.01); *A61B 1/00006* (2013.01); *A61B 1/00188* (2013.01);
(Continued)

(58) Field of Classification Search
CPC .......... A61B 1/00009; A61B 1/06; G02B 7/26
See application file for complete search history.

(56) References Cited

U.S. PATENT DOCUMENTS 4,470,680 A * 9/1984 Inagaki .................. G03B 17/08
                                                                      396/103
6,268,885 B1 * 7/2001 Ohta ...................... G02B 7/102
                                                                      348/335
(Continued)

FOREIGN PATENT DOCUMENTS

JP    H11-309156 A    11/1999
JP    2006-208818 A    8/2006
(Continued)

OTHER PUBLICATIONS

Extended Supplementary European Search Report dated Oct. 17, 2017 in European Patent Application No. 15 74 0320.5.
(Continued)

*Primary Examiner* — Tracy Y. Li
(74) *Attorney, Agent, or Firm* — Scully, Scott, Murphy & Presser, P.C.

(57) ABSTRACT

An endoscope apparatus includes a processor including hardware. The processor implements a focus control process that is implemented by controlling the position of a focus lens included in an optical system that is included in an imaging device, and a mist detection process that detects whether or not mist has occurred. The processor implements the focus control process that stops a focus operation that is performed during the focus control process when the mist detection process has detected that mist has occurred.

19 Claims, 14 Drawing Sheets

(51) Int. Cl.
*G02B 7/04* (2006.01)
*G02B 7/36* (2006.01)
*G06K 9/46* (2006.01)
*G06T 7/00* (2017.01)
*G02B 23/24* (2006.01)
*G03B 13/36* (2006.01)
*H04N 5/225* (2006.01)
*H04N 5/232* (2006.01)
*H04N 5/235* (2006.01)

(52) U.S. Cl.
CPC ............... *A61B 1/127* (2013.01); *G02B 7/04* (2013.01); *G02B 7/36* (2013.01); *G02B 23/243* (2013.01); *G02B 23/2446* (2013.01); *G02B 23/2453* (2013.01); *G03B 13/36* (2013.01); *G06K 9/4642* (2013.01); *G06T 7/0012* (2013.01); *H04N 5/2354* (2013.01); *H04N 5/23212* (2013.01); *G02B 23/2469* (2013.01); *G06T 2207/10068* (2013.01); *H04N 2005/2255* (2013.01)

(56) References Cited

U.S. PATENT DOCUMENTS

| | | | |
|---|---|---|---|
| 7,463,302 B2 | 12/2008 | Kobayashi | |
| 2003/0165333 A1* | 9/2003 | Shinohara | G02B 7/28 396/72 |
| 2003/0184669 A1* | 10/2003 | Nishioka | G02B 7/102 348/335 |
| 2004/0113801 A1* | 6/2004 | Gustafson | A61F 13/2051 340/604 |
| 2007/0027362 A1* | 2/2007 | Handa | A61B 1/00009 600/160 |
| 2008/0221709 A1* | 9/2008 | Ishii | G03F 7/705 700/30 |
| 2011/0302078 A1* | 12/2011 | Failing | B60L 3/00 705/39 |
| 2012/0050769 A1* | 3/2012 | Houjou | G06K 9/00221 358/1.9 |
| 2013/0188029 A1 | 7/2013 | Takahashi | |
| 2013/0286306 A1* | 10/2013 | Eiyama | B41J 29/393 349/19 |

FOREIGN PATENT DOCUMENTS

| | | |
|---|---|---|
| JP | 2006-280425 A | 10/2006 |
| JP | 2010-176061 A | 8/2010 |

OTHER PUBLICATIONS

International Search Report dated Apr. 14, 2015 issued in PCT/JP2015/051305.

* cited by examiner

MIST DETECTION AREA AND AF AREA

IMAGE WHEN USER PERFORMS TREATMENT

MIST DETECTION AREA AND AF AREA

STATE IMMEDIATELY BEFORE MIST OCCURS

STATE IMMEDIATELY AFTER MIST HAS OCCURRED

STATE IN WHICH MIST HAS BECOME THINNER

STATE IN WHICH ABDOMINAL CAVITY IS FILLED WITH MIST

STATE IN WHICH MIST IS NOT DETECTED

MistBd = InpBd - AfBd
NOTE: InpBd IS FREQUENCY BAND
    OF INPUT SIGNAL

ENDOSCOPE APPARATUS AND METHOD FOR OPERATING ENDOSCOPE APPARATUS

CROSS REFERENCE TO RELATED APPLICATION

This application is a continuation of International Patent Application No. PCT/JP2015/051305, having an international filing date of Jan. 20, 2015, which designated the United States, the entirety of which is incorporated herein by reference. Japanese Patent Application No. 2014-009202 filed on Jan. 22, 2014 is also incorporated herein by reference in its entirety.

BACKGROUND

The present invention relates to an endoscope apparatus, a method for operating an endoscope apparatus, and the like.

A depth of field as deep as possible is required for an endoscope apparatus so that the user can easily perform diagnosis and treatment. In recent years, however, an image sensor having a large number of pixels has been used for an endoscope apparatus, and a decrease in depth of field has progressed. In view of this situation, an endoscope apparatus that implements an autofocus (AF) process (operation) has been proposed. The methods described below have been proposed with regard to AF technology that is applied to a video in order to prevent a situation in which a focus operation is unnecessarily performed.

For example, JP-A-2006-208818 discloses a method that stores an AF evaluation value when the focus operation has been completed, and resumes the focus operation when a change equal to or larger than a given threshold value has continued for a time equal to or longer than a given standby time with respect to the AF evaluation value. JP-A-2006-208818 thus prevents a situation in which the focus operation is performed unnecessarily frequently.

JP-A-2010-176061 discloses a method that sets an AF area to the center area of an image, and calculates the degree of similarity in the peripheral area of the image and the degree of similarity in the center area (AF area) of the image from the current image and the previous image after completion of the focus operation. The degree of similarity is a value that decreases as the images are more similar to each other. The focus operation is not performed when the degree of similarity in the peripheral area of the image is equal to or larger than a given threshold value, and the degree of similarity in the center area of the image is equal to or smaller than a given threshold value. JP-A-2010-176061 thus prevents a situation in which the focus operation is unnecessarily performed when the distance to the main object that is situated in the center area of the image does not change even when the object situated in the peripheral area of the image has changed due to a change in framing (after the object has been brought into focus), for example.

It is desirable that an endoscope apparatus be configured so that the field of view is fixed when the user performs treatment, and the focus operation is stopped after the object has been brought into focus.

SUMMARY

According to one aspect of the invention, there is provided an endoscope apparatus comprising:
a processor comprising hardware,
the processor being configured to implement:
a focus control process that is implemented by controlling a position of a focus lens included in an optical system that is included in an imaging device; and
a mist detection process that detects whether or not mist that occurs from an object when treatment using a treatment tool is performed has occurred,
wherein the processor is configured to implement the focus control process that stops a focus operation that is performed during the focus control process when the mist detection process has detected that the mist has occurred.

According to another aspect of the invention, there is provided a method for operating an endoscope apparatus comprising:
performing a focus control process by controlling a position of a focus lens included in an optical system that is included in an imaging device;
detecting whether or not mist that occurs from an object when treatment using a treatment tool is performed has occurred; and
stopping a focus operation that is performed during the focus control process when it has been detected that the mist has occurred.

DESCRIPTION OF EXEMPLARY EMBODIMENTS

Figure 1:
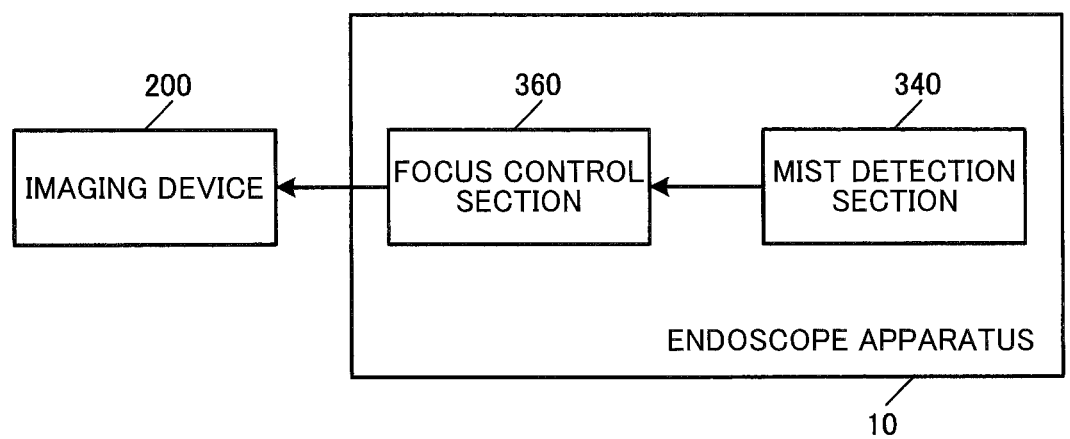
FIG. 1 illustrates a configuration example of an endoscope apparatus according to one embodiment of the invention.

Exemplary embodiments of the invention are described below. Note that the following exemplary embodiments do not in any way limit the scope of the invention laid out in the claims. Note also that all of the elements described below in connection with the exemplary embodiments should not necessarily be taken as essential elements of the invention.

1. Outline

For example, when treatment is performed using an endoscope apparatus (endoscope system) in the surgical field or the like, the user operates the scope so that the lesion is situated in the center area of the image, and performs treatment (e.g., excision or suture) on the lesion using a treatment tool (e.g., electrosurgical knife or forceps). Therefore, it is desirable to set an AF area to the center area of the image in which treatment is performed.

The user performs treatment in a state in which the field of view is fixed. If a change in focus occurs during treatment, it is difficult for the user to perform smooth treatment. Therefore, when the object has been brought into focus in a state in which the field of view is fixed, it is desirable to stop the focus operation in order to prevent a situation in which the image becomes out of focus due to an unintentional change in focus position or an erroneous AF control process, for example.

However, mist may occur within the field of view for the reasons described below, and the focus position may change due to the occurrence of mist.

Specifically, when the user performs treatment, excision, suture, or the like is performed on the lesion (i.e., main object) using an electrosurgical knife, an ultrasonic surgical knife, or the like. When an electrosurgical knife has come in contact with tissue, the lesion area is cauterized due to heat applied by the end of the surgical knife, and ash, smoke, or water vapor is produced, and diffuses within the abdominal cavity. When an ultrasonic surgical knife is used, water contained in tissue diffuses within the abdominal cavity in the form of mist due to cavitation (i.e., a phenomenon in which air bubbles are formed in water due to vibrations). A phenomenon in which such opaque ash, smoke, water vapor, mist, or the like diffuses within the abdominal cavity is referred to as "mist".

When mist has occurred when the user performs treatment, the contrast of the image decreases, and the AF evaluation value acquired from the AF area decreases (i.e., the evaluation value deteriorates) with the passing of time. In such a case, the AF control process cannot determine whether or not the object is in focus based on the AF evaluation value. As a result, the focus lens position changes to a large extent, and the image becomes out of focus (defocused). Moreover, a change in magnification occurs due to a change in focus lens position. As a result, an image having poor visibility is provided to the user who performs treatment. When the focus lens position has changed to a large extent from the in-focus position, it takes time to bring the object into focus even when mist has disappeared, and it has become possible to implement a normal AF operation.

JP-A-2006-208818 and JP-A-2010-176061 disclose technology that suppresses or reduces a situation in which the AF operation is unnecessarily performed. However, since the technology disclosed in JP-A-2006-208818 and JP-A-2010-176061 does not take account of the occurrence of mist, the technology disclosed in JP-A-2006-208818 and JP-A-2010-176061 cannot accurately suppress or reduce a situation in which the AF operation is unnecessarily performed when mist has occurred. Therefore, it is difficult to stop the focus operation when (while) the user performs treatment.

FIG. 1 illustrates a configuration example of an endoscope apparatus according to several embodiments of the invention that can solve the above problem. An endoscope apparatus 10 includes a focus control section 360 that performs a focus control process by controlling the position of a focus lens included in an optical system that is included in an imaging device 200, and a mist detection section 340 that detects whether or not mist has occurred. The focus control section 360 stops a focus operation that is performed during the focus control process when the mist detection section 340 has detected that mist has occurred.

Since the parameter (e.g., brightness value, saturation value, and contrast value) of the image changes with the passing of time when mist has occurred (as described later with reference to FIGS. 7A to 10, for example), the occurrence of mist can be detected by detecting a change in parameter from the image. Note that whether or not mist has occurred may be detected by utilizing control information (e.g., ON state) about the treatment tool that causes mist to occur instead of merely detecting whether or not mist has occurred from the image.

The focus operation automatically brings the object into focus (AF control process) using a contrast method, a phase detection method (e.g., pupil division phase detection method or image plane phase detection method), or the like. Specifically, the term "focus control process" used herein refers to a process that controls the position of the focus lens (including a process that continuously stops the focus lens), and an operation that is performed during the focus control process, and brings the object into focus is referred herein to as "focus operation". When the focus control section 360 has stopped the focus operation, the focus control section 360 stops moving the focus lens to fix the focus position.

It is possible to suppress or reduce a situation in which an erroneous AF operation is performed due to mist by thus stopping the focus operation when it has been detected that mist has occurred. Specifically, it is possible to stop the focus operation during a period in which the user performs treatment. This makes it possible to prevent a situation in which the image becomes out of focus due to an unintentional change in focus position or an erroneous AF control process, for example.

The endoscope apparatus according to the embodiments of the invention may be configured as described below. Specifically, the endoscope apparatus may include a memory that stores information (e.g., a program and various types of data), and a processor (i.e., a processor including hardware) that operates based on the information stored in the memory. The processor implements a focus control process that is implemented by controlling the position of the focus lens included in the optical system that is included in the imaging device 200, and a mist detection process that detects whether or not mist has occurred. The processor stops the focus operation that is performed during the focus control process when the mist detection process has detected that mist has occurred.

The processor may implement the function of each section by individual hardware, or may implement the function of each section by integrated hardware, for example. The processor may be a central processing unit (CPU), for example. Note that the processor is not limited to a CPU. Various other processors such as a graphics processing unit (GPU) or a digital signal processor (DSP) may also be used. The processor may be a hardware circuit that includes an ASIC. The memory may be a semiconductor memory (e.g., SRAM or DRAM), a register, a magnetic storage device (e.g., hard disk drive), or an optical storage device (e.g., optical disk device). For example, the memory stores a computer-readable instruction, and each section (e.g., focus control section 360 and mist detection section 340 illustrated in FIG. 1) of the endoscope apparatus is implemented by causing the processor to execute the instruction. The instruction may be an instruction included in an instruction set that is included in a program, or may be an instruction that causes a hardware circuit included in the processor to operate. Each section of the endoscope apparatus refers to the focus control section 360 and the mist detection section 340 illustrated in FIG. 1. Alternatively, each section of the endoscope apparatus refers to the pre-processing section 320, the image processing section 330, the mist detection section 340, the control section 350, and the focus control section 360 illustrated in FIG. 2.

The operation according to the embodiments of the invention is implemented as described below, for example. An image captured by the imaging device 200 is stored in the memory. The processor generates a signal that controls the position of the focus lens based on the captured image read from the memory, and outputs the signal to the focus lens driver section to control the position of the focus lens, for example. The processor performs a process that detects whether or not mist has occurred based on the captured image read from the memory, various types of control information, or the like, and stores information that represents whether or not mist has occurred in the memory, for example. The processor reads the information that represents whether or not mist has occurred from the memory, and stops the focus operation that is performed during the focus control process when the information represents that mist has occurred.

Each section of the endoscope apparatus is implemented as a module of a program that operates on the processor. For example, the focus control section 360 is implemented as a focus control module that implements the focus control process that is implemented by controlling the position of the focus lens included in the optical system that is included in the imaging device 200. The mist detection section 340 is implemented as a mist detection module that detects whether or not mist has occurred. The focus control module stops the focus operation that is performed during the focus control process when the mist detection module has detected that mist has occurred.

2. First Embodiment 2.1. Endoscope Apparatus

Figure 2:
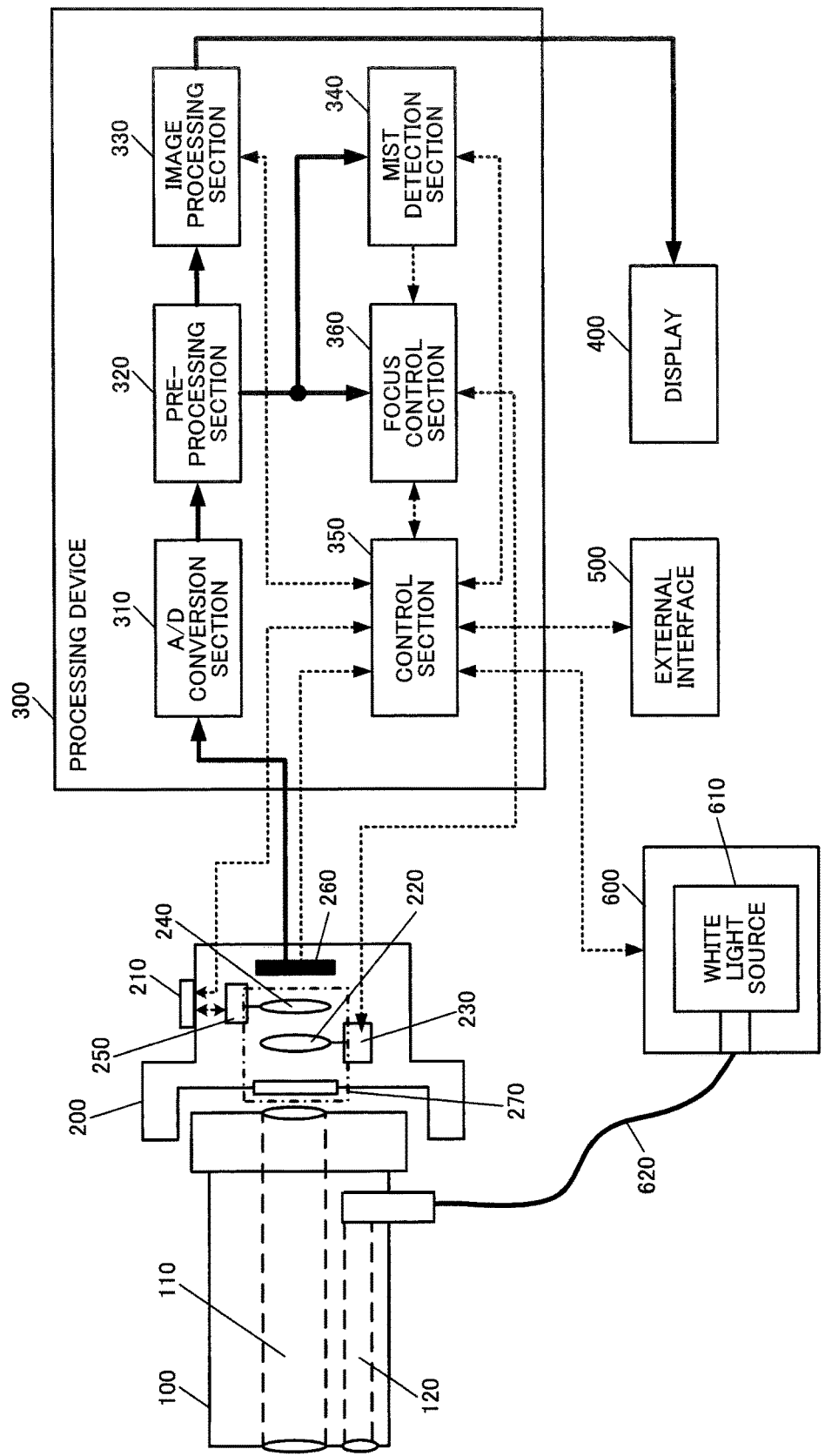
FIG. 2 illustrates a configuration example of an endoscope apparatus (first embodiment).

A first embodiment of the invention is described in detail below. FIG. 2 illustrates a configuration example of an endoscope apparatus according to the first embodiment. The endoscope apparatus includes a rigid scope 100 that is an insertion section that is inserted into a body, an imaging device 200 that is connected to the rigid scope 100, a processing device 300, a display 400, an external interface (I/F) 500, and a light source device 600.

The light source device 600 includes a white light source 610 that emits (generates) white light, and a light guide cable 620 that guides the light emitted from the white light source 610 to the rigid scope 100.

The rigid scope 100 includes a lens system 110 that includes an imaging lens, a relay lens, an eyepiece, and the like, and a light guide section 120 that guides the light output from the light guide cable 620 to the end of the rigid scope 100.

The imaging device 200 includes an objective lens system (optical system) 270 that focuses the light output from the lens system 110. The objective lens system 270 includes a focus lens 220 that adjusts the in-focus object plane position, and a zoom lens 240 that adjusts the optical magnification.

The imaging device 200 also includes an image sensor 260 that photoelectrically converts the reflected light focused by the objective lens system 270 to generate an image, a focus lens driver section 230 that drives the focus lens 220, a zoom lens driver section 250 that drives the zoom lens 240, and a zoom button 210 that is used to adjust the zoom lens position. The focus lens driver section 230 and the zoom lens driver section 250 are implemented by a voice coil motor (VCM), for example. The image sensor 260 is a solid-state image sensor that includes a Bayer color filter array, for example.

Note that the term "in-focus object plane position" used herein refers to a position at which the object is brought into focus. Specifically, the term "in-focus object plane position" used herein refers to the position of the object when the object is brought into focus on the image sensor 260 through the objective lens system 270. The in-focus object plane position is represented by the distance from a reference position (e.g., the position of the objective lens system 270 or the image sensor 260) of the imaging device 200 to the object, for example.

The processing device 300 includes an A/D conversion section 310, a pre-processing section 320, an image processing section 330, a focus control section 360, a control section 350, and a mist detection section 340.

The A/D conversion section 310 converts an analog signal sequentially output from the image sensor 260 into a digital image, and sequentially outputs the digital image to the pre-processing section 320. The pre-processing section 320 performs image processing (e.g., white balance process, interpolation process (demosaicing process), and YCbCr conversion process) on the image output from the A/D conversion section 310, and sequentially outputs the resulting image to the image processing section 330 and the focus control section 360.

The image processing section 330 performs image processing (e.g., color conversion process, grayscale transformation process, edge enhancement process, and noise reduction process) on the image output from the pre-processing section 320, and sequentially outputs the resulting image to the display 400. The display 400 is a liquid crystal monitor, for example. The display 400 displays the image sequentially output from the image processing section 330.

The mist detection section 340 detects whether or not mist has occurred, and whether or not mist has disappeared, based on the image output from the pre-processing section 320. The focus control section 360 controls the focus lens driver section 230 based on the image output from the pre-processing section 320 to control the focus operation that brings the object into focus. The focus control section 360 stops or resumes the focus operation when the occurrence of mist or the disappearance of mist has been detected. The details of the mist detection section 340 and the focus control section 360 are described later.

The control section 350 is bidirectionally connected to each section (e.g., external interface 500, image processing section 330, focus control section 360, image sensor 260, and zoom button 210) of the endoscope apparatus, and exchanges a control signal with each section of the endoscope apparatus.

The external interface 500 is an interface that allows the user to perform an input to the endoscope apparatus, for example. For example, the external interface 500 includes an AF button (AF start/stop button), an adjustment button for adjusting an image processing parameter, a switch for setting a treatment tool (electrosurgical knife or ultrasonic surgical knife) to an ON state or an OFF state, and the like.

ON/OFF information about the treatment tool (i.e., information that represents the ON/OFF state of the switch) is transmitted to the control section 350.

2.2. Mist Detection Section and Focus Control Section

Figure 3:
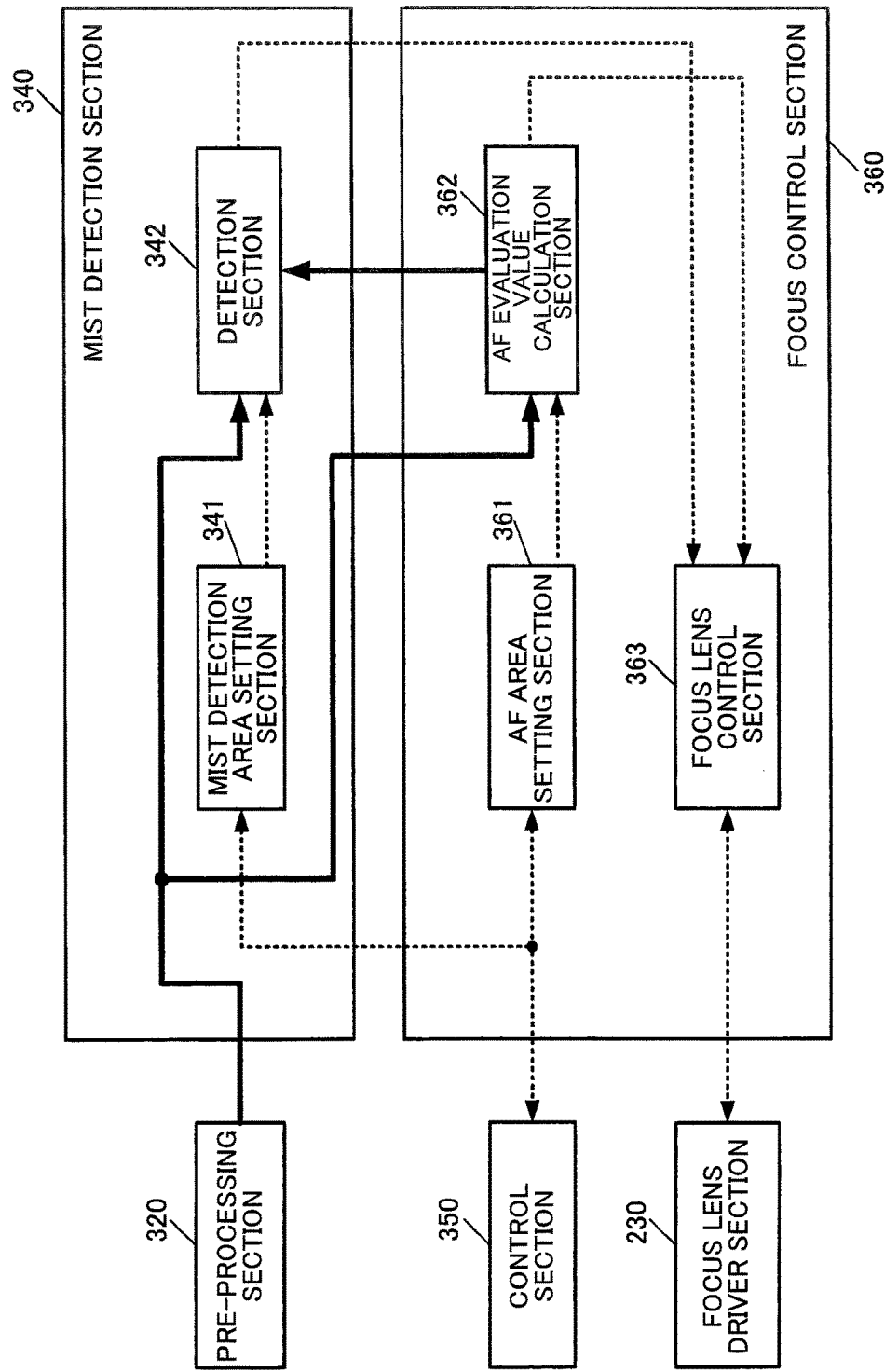
FIG. 3 illustrates a detailed configuration example of a mist detection section and a focus control section (first embodiment).

FIG. 3 illustrates a detailed configuration example of the mist detection section 340 and the focus control section 360. The mist detection section 340 includes a mist detection area setting section 341 and a detection section 342. The focus control section 360 includes an AF area setting section 361, an AF evaluation value calculation section 362, and a focus lens control section 363.

The mist detection area setting section 341 sets a mist detection area (see FIG. 4) based on information (e.g., image size information) output from the control section 350, for example. The mist detection area setting section 341 outputs mist detection area information (i.e., information about the mist detection area that has been set by the mist detection area setting section 341) to the detection section 342. For example, the mist detection area setting section 341 divides the image into 3×3 areas to set nine evaluation blocks, and sets a set of the nine evaluation blocks to be the mist detection area. Note that the number of evaluation blocks set to be the mist detection area can be set arbitrarily.

The detection section 342 detects whether or not mist has occurred based on the mist detection area information output from the mist detection area setting section 341, and the image sequentially output from the pre-processing section 320. The detection section 342 outputs mist detection information that represents whether or not mist has been detected to the focus lens control section 363. The details of the mist detection method are described later.

The AF area setting section 361 sets an AF area (see FIG. 4) based on the information (e.g., image size information) output from the control section 350, for example. The AF area setting section 361 outputs AF area information (i.e., information about the AF area that has been set by the AF area setting section 361) to the AF evaluation value calculation section 362. In the first embodiment, an area that is identical to the center evaluation block among a plurality of evaluation blocks set to be the mist detection area is set to be the AF area for convenience of explanation. Since the size of the evaluation block and the size of the AF area need not necessarily be identical to each other, an area having a size differing from that of the evaluation block may be set to be the AF area in the center area of the image.

The AF evaluation value calculation section 362 calculates an AF evaluation value based on the AF area information output from the AF area setting section 361, and the image sequentially output from the pre-processing section 320. For example, the AF evaluation value calculation section 362 calculates a Y signal of each pixel included in the AF area, performs an arbitrary band-pass filtering (BPF) process on the Y signal, and calculates the sum of the outputs from the BPF process to be the AF evaluation value. The AF evaluation value calculation section 362 sequentially outputs the calculated AF evaluation value to the focus lens control section 363.

The focus lens control section 363 generates control information about the focus lens based on the mist detection information output from the detection section 342 and the AF evaluation value output from the AF evaluation value calculation section 362, and outputs the control information to the focus lens driver section 230. The focus lens driver section 230 drives the focus lens based on the control information output from the focus lens control section 363.

2.3. Focus Control Process

Figure 5:
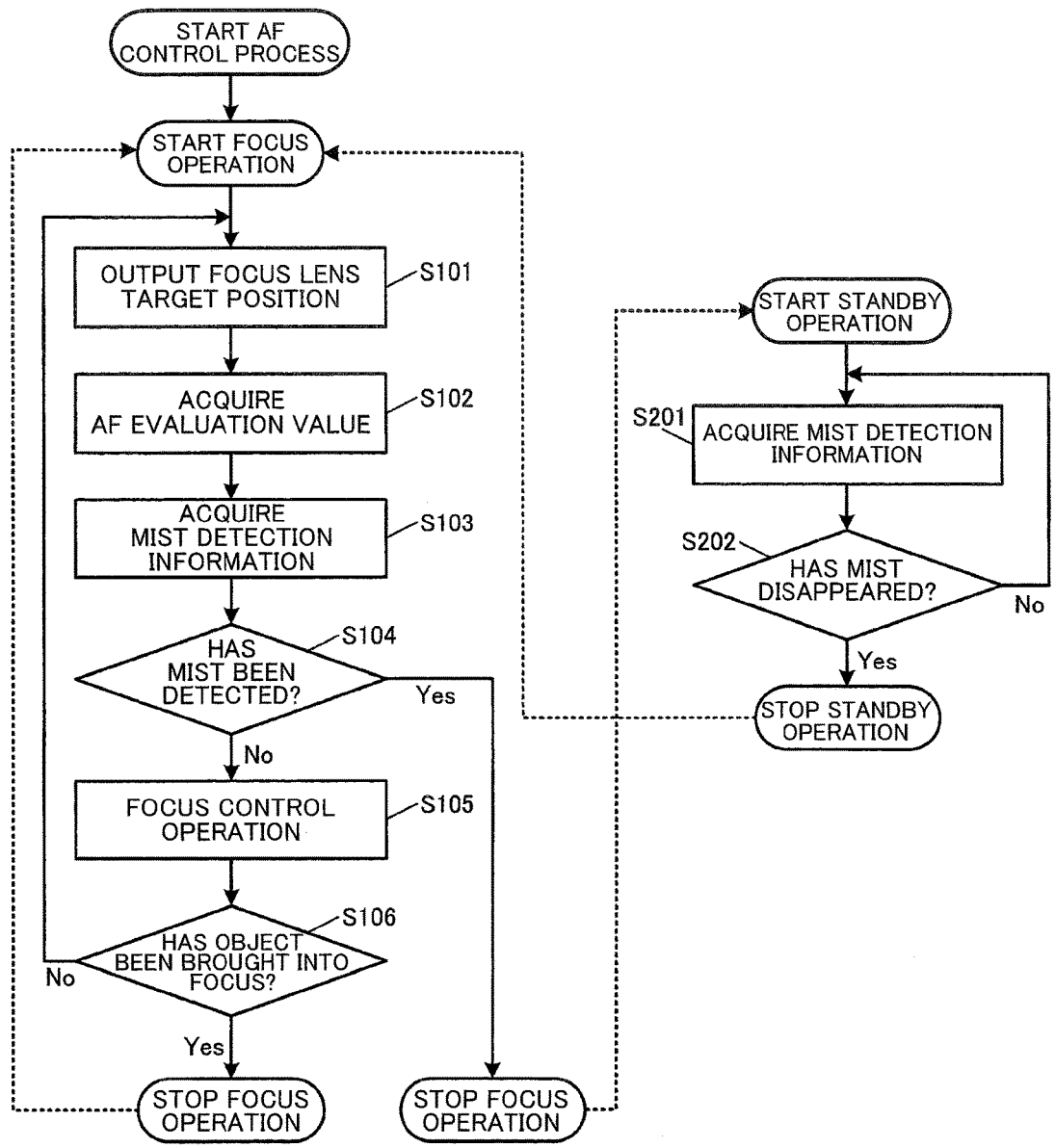
FIG. 5 is a flowchart of a process performed by a mist detection section and a focus control section.

FIG. 5 illustrates a flowchart of the focus control process when the mist detection process is performed as described above.

When the AF control process has started, the focus lens control section 363 starts the focus operation. The focus lens control section 363 performs the focus operation using known AF technology. For example, the focus lens control section 363 performs the focus operation using a known peak detection control process (e.g., contrast AF operation).

In the first embodiment, the focus control section 360 determines the focus lens position (target position) for acquiring the AF evaluation value, and outputs the target position to the focus lens driver section 230 (step S101). The focus lens driver section 230 moves the focus lens to the target position. The focus lens control section 363 acquires the AF evaluation value that corresponds to the target position from the AF evaluation value calculation section 362 (step S102). The focus control section 360 then acquires the mist detection information from the detection section 342 included in the mist detection section 340 (step S103).

The focus control section 360 determines whether or not mist has occurred based on the mist detection information (step S104). When the focus control section 360 has determined that mist has not occurred, the focus control section 360 performs the focus control operation based on the AF evaluation value (step S105), and determines whether or not the object has been brought into focus (step S106). When the focus control section 360 has determined that the object has not been brought into focus, the focus control section 360 performs the step S101 again. When the focus control section 360 has determined that the object has been brought into focus, the focus control section 360 stops the focus operation. The focus control section 360 then starts the focus operation again. When the focus control section 360 has determined that mist has occurred in the step S104, the focus control section 360 stops the focus operation without performing the focus control operation.

When the focus control section 360 has determined that mist has occurred in the step S104, and stopped the focus operation, the focus lens control section 363 starts a standby operation. Specifically, the focus lens control section 363 acquires the mist detection information output from the detection section 342 (step S201). The focus lens control section 363 then determines whether or not the mist has disappeared based on the mist detection information (step S202). When the focus lens control section 363 has determined that the mist has not disappeared, the focus lens control section 363 performs the step S201 again. When the focus lens control section 363 has determined that the mist has disappeared, the focus lens control section 363 stops the standby operation.

When the focus lens control section 363 has stopped the standby operation, the focus lens control section 363 starts the AF control process again. Specifically, the focus lens control section 363 continuously outputs an identical focus lens position (i.e., the focus lens is not driven) during a period in which the focus lens control section 363 performs the standby operation in response to the detection of mist. For example, the focus lens control section 363 continuously outputs the target position when the focus operation was stopped to the focus lens driver section 230. Note that the AF control process is started based on whether or not a predetermined state has occurred (e.g., triggered by scene detection) (details thereof are omitted).

2.4. Mist Detection Process

Figure 4:
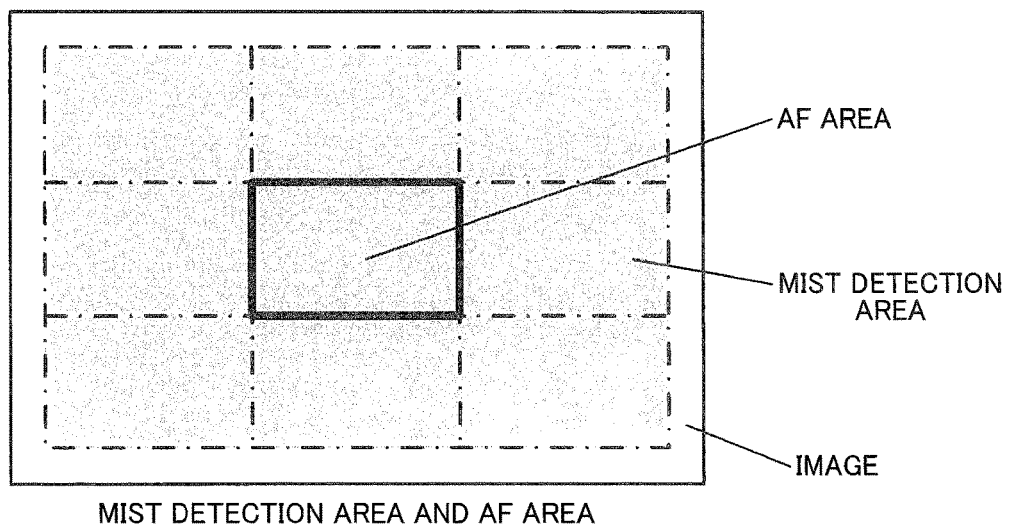
FIG. 4 illustrates an example of a method that sets a mist detection area and an AF area.

The mist detection process is described in detail below. The mist detection area illustrated in FIG. 4 is set for the reasons described below.

Figure 6:
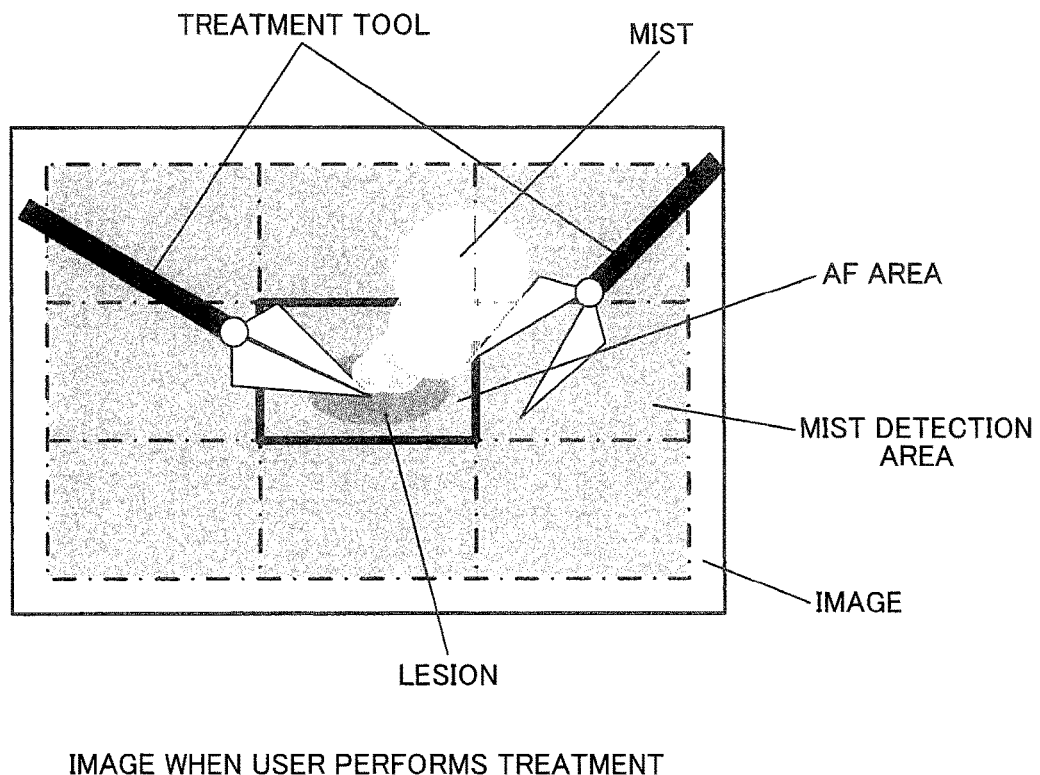
FIG. 6 illustrates an example of an image when a user performs treatment.

FIG. 6 is a view illustrating a typical image that is acquired by the endoscope apparatus while the user performs treatment. As described above, it is desirable to set the AF area to the center area of the image since the user performs treatment in the center area of the field of view. Since mist occurs due to treatment, the occurrence frequency of mist becomes a maximum in (around) the AF area. Therefore, it is difficult to accurately stop the focus operation when the user performs treatment using only the information (e.g., AF evaluation value) acquired from the AF area within the image.

For example, when a change in contrast has been detected in the AF area, it is difficult to determine whether the change in contrast has occurred due to the occurrence of mist or a change in focus. Specifically, it is difficult to determine whether or not mist has occurred (i.e., determine whether or not to stop the focus operation) from a change in contrast in the AF area.

On the other hand, a change in image when mist has occurred differs between the peripheral area of the image and the center area of the image. Specifically, since the field of view is fixed when the user performs treatment so that the lesion is situated in the center area of the image, and the user performs treatment on the lesion that is situated in the center area of the image, mist does not occur in the peripheral area of the image since treatment is not performed within the peripheral area of the image. Therefore, when mist has occurred in the center area of the image, a change in image is relatively small in the peripheral area of the image until the mist reaches the peripheral area of the image.

According to the first embodiment, an area that includes the AF area and the peripheral area of the image is set to be the mist detection area (i.e., the mist detection area also includes an area that differs from the AF area) (see FIG. 4), and the focus operation is controlled (i.e., the focus operation is started or stopped) using the mist detection information acquired from the mist detection area. It is possible to utilize the characteristics of mist that diffuses from the center area of the image to the peripheral area of the image by detecting the occurrence of mist from the information about the center area and the peripheral area of the image. This makes it possible to accurately detect the occurrence of mist independently of a change in image due to a change in focus. Therefore, it is possible to cause the endoscope apparatus to perform the focus operation only when mist is absent in the scene observed by the user, and the focus adjustment process is necessary.

A method that detects the occurrence of mist, and a method that detects the disappearance of mist are described in detail below.

Each of a plurality of blocks set to be the mist detection area is referred to as "block b[i]". i is a block number that is linked to each block. In the example illustrated in FIG. 4, i=0, 1, . . . , 8. The detection section 342 calculates the average brightness b_Y[i][n], the average saturation b_S[i][n], and the D range b_D[i][n] of each block b[i] from the current image, and stores the average brightness b_Y[i][n], the average saturation b_S[i][n], and the D range b_D[i][n] in a memory (not illustrated in the drawings). Note that n is the image acquisition timing.

The detection section 342 then calculates mist detection evaluation values Vy[n], Vs[n], and Vd[n] using the following expressions (1) to (3). Note that b_Y[i][n-x] is the average brightness of each block calculated from an image acquired at a timing earlier than the acquisition timing of the current image by x frames, b_S[i][n-x] is the average saturation of each block calculated from an image acquired at a timing earlier than the acquisition timing of the current image by x frames, and b_D[i][n-x] is the D range of each block calculated from an image acquired at a timing earlier than the acquisition timing of the current image by x frames. Note that x is an arbitrary number.

$$Vy[n] = \sum_i (b\_Y[i][n] - b\_Y[i][n-x]) \quad (1)$$

$$Vs[n] = \sum_i (b\_S[i][n] - b\_S[i][n-x]) \quad (2)$$

$$Vd[n] = \sum_i (b\_D[i][n] - b\_D[i][n-x]) \quad (3)$$

As is clear from the expressions (1) to (3), the evaluation value Vy[n] is calculated by calculating the sum of the difference between the average brightness of each evaluation block calculated from the current image (time n) and the average brightness of each evaluation block calculated from an image acquired at a timing earlier than the acquisition timing of the current image by x frames, the evaluation value Vs[n] is calculated by calculating the sum of the difference between the average saturation of each evaluation block calculated from the current image (time n) and the average saturation of each evaluation block calculated from an image acquired at a timing earlier than the acquisition timing of the current image by x frames, and the evaluation value Vd[n] is calculated by calculating the sum of the difference between the D range of each evaluation block calculated from the current image (time n) and the D range of each evaluation block calculated from an image acquired at a timing earlier than the acquisition timing of the current image by x frames.

A temporal change in the evaluation values Vy[n], Vs[n], and Vd[n] is described below with reference to FIGS. 7A to 15. FIGS. 7A to 7F are views schematically illustrating a temporal change in image during a period from the occurrence of mist to the disappearance of mist.

Figure 7A:
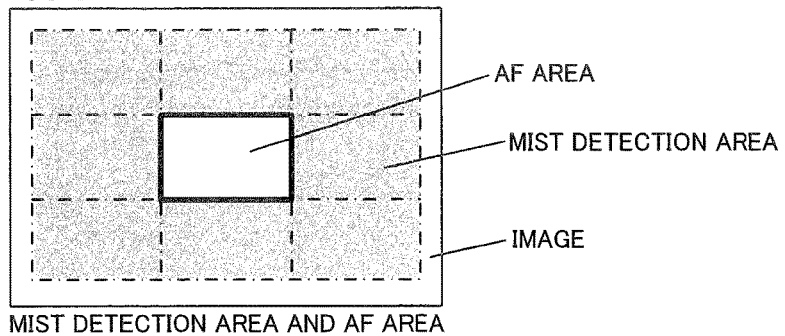
FIGS. 7A to 7F illustrate an example of a temporal change in image due to mist.
Figure 7B:
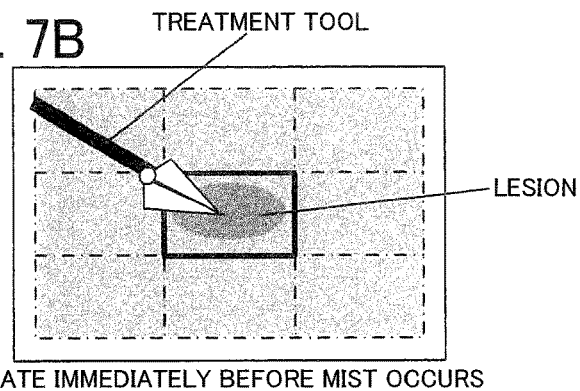
Figure 7C:
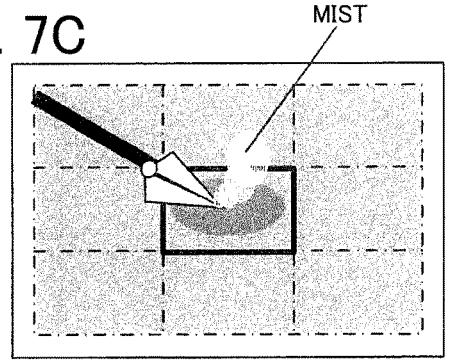
Figure 7E:
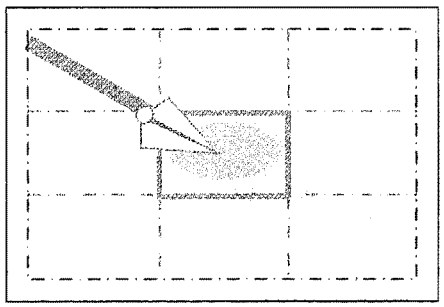
Figure 7D:
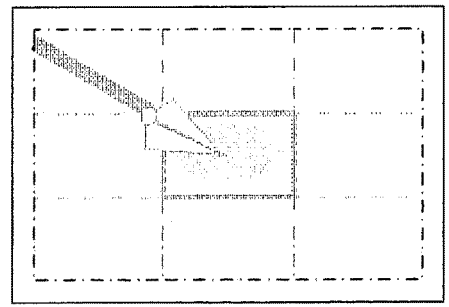
Figure 7F:
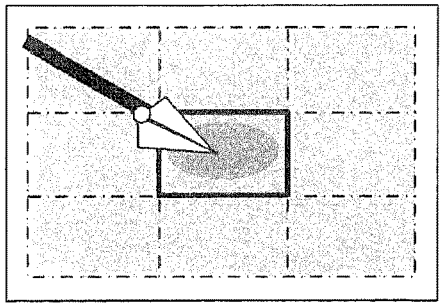

FIG. 7A illustrates the mist detection area and the AF area. FIG. 7B illustrates a state in which a treatment tool is placed in a state in which a lesion is situated in the AF area, and treatment is performed. FIG. 7C illustrates a state in which mist has occurred from the center area of the image in which treatment is performed. FIG. 7D illustrates a state in which the mist spreads (diffuses) toward the peripheral area of the image, and the abdominal cavity has been filled with the mist. This state continues until the mist disappears (although the mist concentration may change). FIG. 7E illustrates a state in which the occurrence of mist has stopped, and the mist has become thinner. FIG. 7F illustrates a state in which the mist has disappeared, and the AF operation can be performed again.

Figure 8:
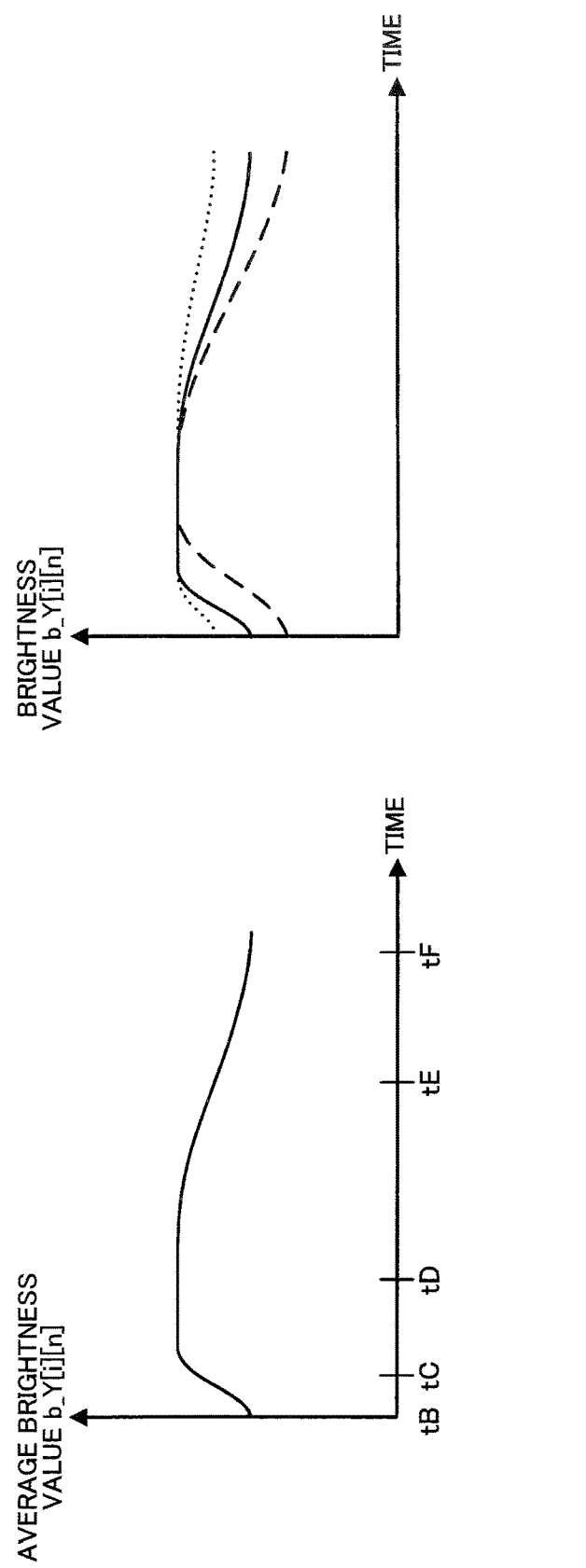
FIG. 8 illustrates an example of a temporal change in brightness value due to the occurrence of mist.
Figure 9:
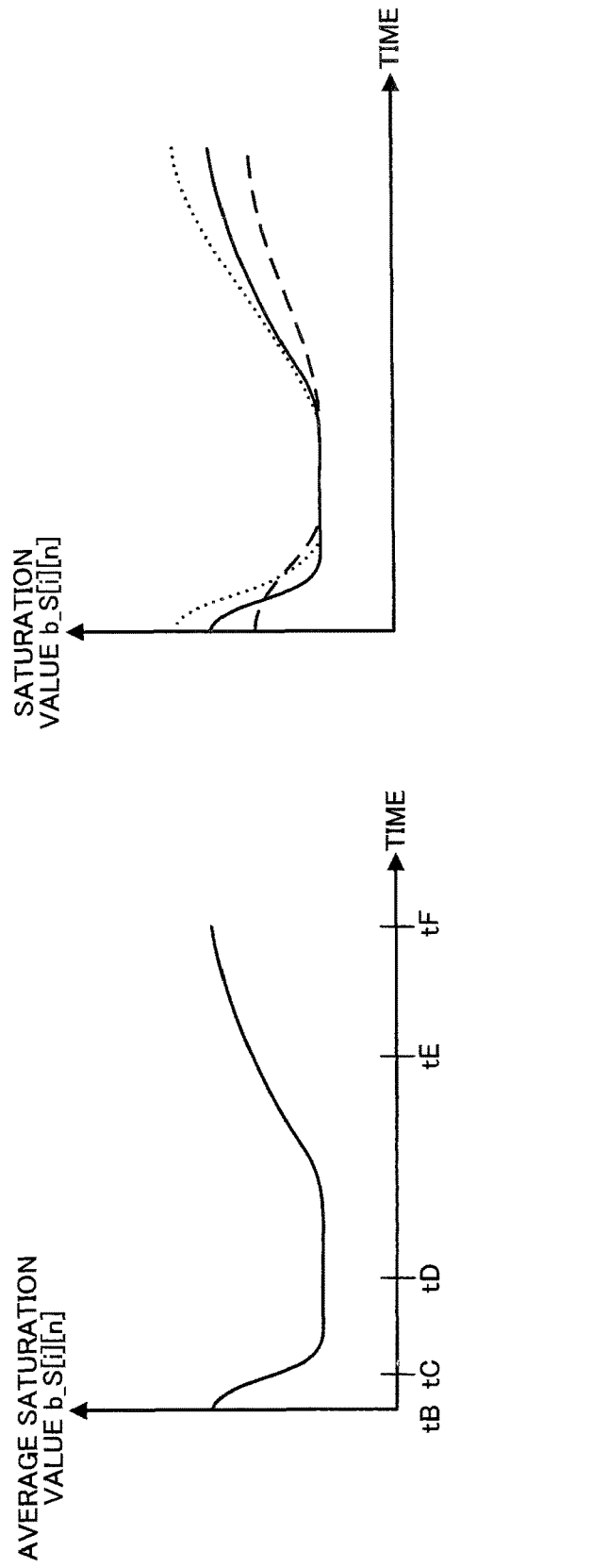
FIG. 9 illustrates an example of a temporal change in saturation value due to the occurrence of mist.
Figure 10:
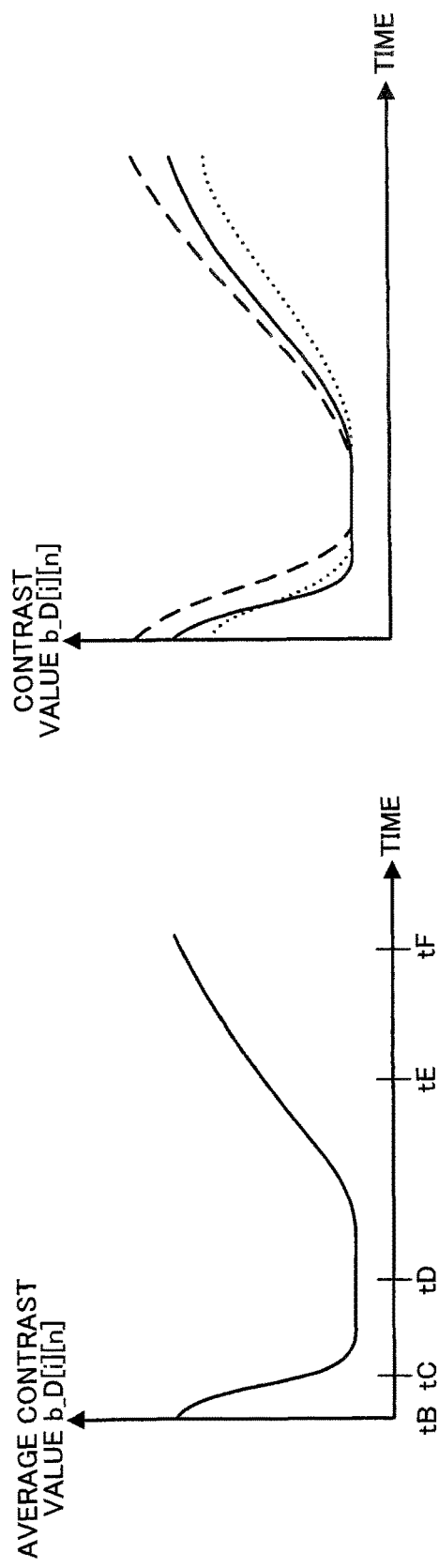
FIG. 10 illustrates an example of a temporal change in contrast value due to the occurrence of mist.

FIGS. 8 to 10 are views illustrating a change in the brightness value, the saturation value, and the contrast value of the image when a change in mist occurs as described above. In FIGS. 8 to 10, the right graph illustrates the value of each block, and the left graph illustrates the average value of all of the blocks. The times tB to tF correspond to the timings illustrated in FIGS. 7B to 7F, respectively.

As illustrated in FIGS. 8 to 10, when mist has occurred, the brightness value increases, and the saturation value and the contrast value (D range) decrease as the abdominal cavity is filled with the mist. When the occurrence of mist has stopped, the brightness value decreases, and the saturation value and the contrast value increase as the mist disappears. Specifically, when mist has occurred, the brightness value increases since the mist causes diffused reflection of illumination light, and the saturation value and the contrast value decrease since the mist is opaque.

Figure 11:
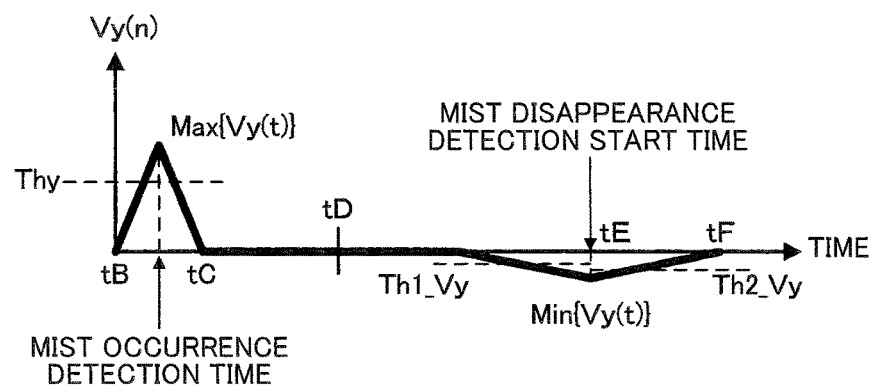
FIG. 11 illustrates an example of a temporal change in brightness evaluation value due to the occurrence of mist.
Figure 12:
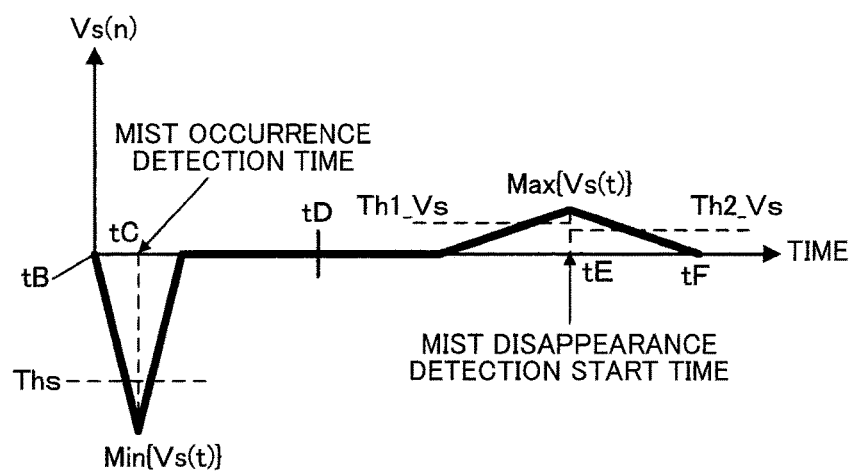
FIG. 12 illustrates an example of a temporal change in saturation evaluation value due to the occurrence of mist.
Figure 13:
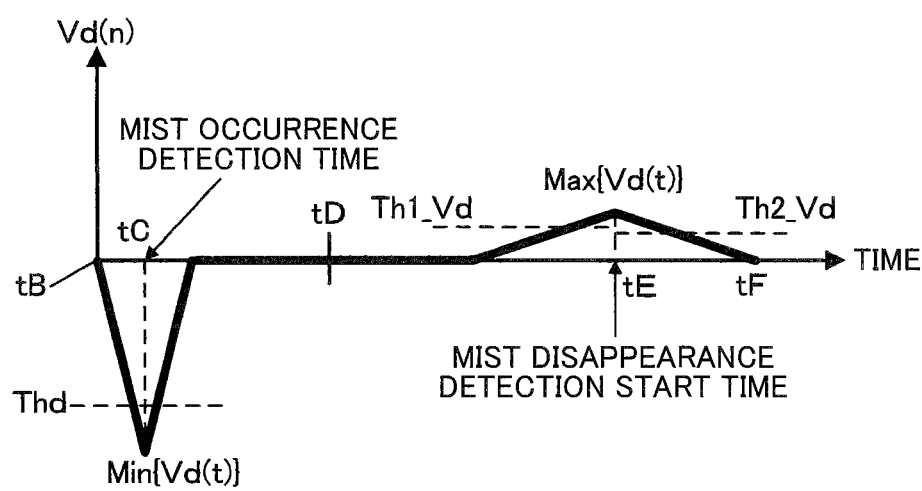
FIG. 13 illustrates an example of a temporal change in contrast evaluation value due to the occurrence of mist.

FIGS. 11 to 13 are views illustrating a change in the evaluation values Vy[n], Vs[n], and Vd[n] when the brightness value, the saturation value, and the contrast value change as described above. Since the evaluation values Vy[n], Vs[n], and Vd[n] are differential values, the evaluation values Vy[n], Vs[n], and Vd[n] have characteristics obtained by the differentiation of the characteristics illustrated in FIGS. 8 to 10.

As illustrated in FIGS. 11 to 13, when mist has occurred, the evaluation value Vy[n] has characteristics that protrude upward since the brightness value has a positive slope, and the evaluation values Vs[n] and Vd[n] have characteristics that protrude downward since the saturation value and the contrast value have a negative slope. When the mist disappears, the evaluation value Vy[n] (brightness evaluation value) has characteristics that protrude downward, and the evaluation value Vs[n] (saturation evaluation value) and the evaluation value Vd[n] (contrast evaluation value) have characteristics that protrude upward.

In the first embodiment, whether or not mist has occurred is determined as described below with respect to a change in the evaluation values Vy[n], Vs[n], and Vd[n].

Specifically, the detection section 342 determines that mist has occurred at a time n (between the times tB and tC in FIGS. 11 to 13) at which the evaluation value Vy[n] (brightness evaluation value) has become larger than a given threshold value Thy, the evaluation value Vs[n] (saturation evaluation value) has become smaller than a given threshold value Ths, and the evaluation value Vd[n] (contrast evaluation value) has become smaller than a given threshold value Thd.

Alternatively, the detection section 342 may detect a time at which the evaluation value Vy[n] (brightness evaluation value) has reached a maximum value Max{Vy}, a time at which the evaluation value Vs[n] (saturation evaluation value) has reached a minimum value Min{Vs}, and a time at which the evaluation value Vd[n] (contrast evaluation value) has reached a minimum value Min{Vd}, and determine that mist has occurred at a time n (time tC in FIGS. 11 to 13) when the detected times (almost) coincide with each other.

Whether or not the mist has disappeared is then determined using the evaluation values Vy[n], Vs[n], and Vd[n].

Specifically, the detection section 342 detects a time at which the evaluation value Vy[n] (brightness evaluation value) has reached a minimum value Min{Vy} on condition that the evaluation value Vy[n] (brightness evaluation value) is smaller than a given first threshold value Th1_Vy, a time at which the evaluation value Vs[n] (saturation evaluation value) has reached a maximum value Max{Vs} on condition that the evaluation value Vs[n] (saturation evaluation value) is larger than a given first threshold value Th1_Vs, and a time at which the evaluation value Vd[n] (contrast evaluation value) has reached a maximum value Max{Vd} on condition that the evaluation value Vd[n] (contrast evaluation value) is larger than a given first threshold value Th1_Vd (time tE in FIGS. 11 to 13). The detection section 342 determines that the mist has disappeared at a time n (between the times tE and tF in FIGS. 11 to 13) at which the evaluation value Vy[n] (brightness evaluation value) has become larger than a given second threshold value Th2_Vy after the evaluation value Vy[n] (brightness evaluation value) has reached the minimum value Min{Vy}, the evaluation value Vs[n] (saturation evaluation value) has become smaller than a given second threshold value Th2_Vs after the evaluation value Vs[n] (saturation evaluation value) has reached the maximum value Max{Vs}, and the evaluation value Vd[n] (contrast evaluation value) has become smaller than a given second threshold value Th2_Vd after the evaluation value Vd[n] (contrast evaluation value) has reached the maximum value Max{Vd}.

Since the detection section 342 determines that the mist has disappeared when the evaluation values Vy[n], Vs[n], and Vd[n] have reached the given second threshold value after the maximum value or the minimum value has been reached, it is possible to resume the AF control process when the contrast in the AF area has increased (i.e., the mist has disappeared) to such an extent that the AF control process can be performed.

Alternatively, the detection section 342 may determine that the mist has disappeared at a time n (time tE in FIGS. 11 to 13) at which the evaluation value Vy[n] (brightness evaluation value) has reached the minimum value Min{Vy} on condition that the evaluation value Vy[n] (brightness evaluation value) is smaller than the given first threshold value Th1_Vy, the evaluation value Vs[n] (saturation evaluation value) has reached the maximum value Max{Vs} on condition that the evaluation value Vs[n] (saturation evaluation value) is larger than the given first threshold value Th1_Vs, and the evaluation value Vd[n] (contrast evaluation value) has reached the maximum value Max{Vd} on condition that the evaluation value Vd[n] (contrast evaluation value) is larger than the given first threshold value Th1_Vd.

The detection section 342 outputs the mist occurrence determination result and the mist disappearance determination result to the focus lens control section 363 as the mist detection information.

2.5. Second Mist Detection Method

Note that the mist detection method is not limited to the above method. For example, the evaluation values Vy[n], Vs[n], and Vd[n] may be calculated using the following expressions (4) to (6).

$$Vy[n] = \text{Max } A(b\_Y[i][n] - b\_Y[i][n-x]) \tag{4}$$

$$Vs[n] = \text{Max } A(b\_S[i][n] - b\_S[i][n-x]) \tag{5}$$

$$Vd[n] = \text{Max } A(b\_D[i][n] - b\_D[i][n-x]) \tag{6}$$

Note that MaxA( ) acquires a value among values in parentheses that has the maximum absolute value. The maximum value is determined using the absolute value, but the acquired value is signed. Specifically, the evaluation value Vy[n] is a signed value (signed absolute value) at which the absolute value of the difference between the average brightness of each evaluation block calculated from the current image (time n) and the average brightness of each evaluation block calculated from an image acquired at a timing earlier than the acquisition timing of the current image by x frames, becomes a maximum. The evaluation value Vs[n] is a signed value (signed absolute value) at which the absolute value of the difference between the average saturation of each evaluation block calculated from the current image (time n) and the average saturation of each evaluation block calculated from an image acquired at a timing earlier than the acquisition timing of the current image by x frames, becomes a maximum. The evaluation value Vd[n] is a signed value (signed absolute value) at which the absolute value of the difference between the D range of each evaluation block calculated from the current image (time n) and the D range of each evaluation block calculated from an image acquired at a timing earlier than the acquisition timing of the current image by x frames, becomes a maximum.

The expressions (4) to (6) use the evaluation value of a block among a plurality of evaluation blocks in which the largest change has occurred. There is a tendency that mist localizes. It is considered that the largest change in evaluation value occurs in an area in which mist localizes. Therefore, it is possible to detect a state in which mist localizes with higher sensitivity by utilizing the largest change as the evaluation value.

2.6. Third Mist Detection Method

Evaluation values Vyσ[n], Vsσ[n], and Vdσ[n] may be calculated using the following expressions (7) to (9).

$$Vy\sigma[n]=\text{Sigma}(b\_Y[i][n]-b\_Y[i][n-x]) \quad (7)$$

$$Vs\sigma[n]=\text{Sigma}(b\_S[i][n]-b\_S[i][n-x]) \quad (8)$$

$$Vd\sigma[n]=\text{Sigma}(b\_D[i][n]-b\_D[i][n-x]) \quad (9)$$

Note that Sigma( ) acquires the standard deviation of the values in parentheses. Specifically, the evaluation value Vyσ[n] is the standard deviation within all of the evaluation blocks with respect to the difference between the average brightness of each evaluation block calculated from the current image (time n) and the average brightness of each evaluation block calculated from an image acquired at a timing earlier than the acquisition timing of the current image by x frames. The evaluation value Vsσ[n] is the standard deviation within all of the evaluation blocks with respect to the difference between the average saturation of each evaluation block calculated from the current image (time n) and the average saturation of each evaluation block calculated from an image acquired at a timing earlier than the acquisition timing of the current image by x frames. The evaluation value Vdσ[n] is the standard deviation within all of the evaluation blocks with respect to the difference between the D range of each evaluation block calculated from the current image (time n) and the D range of each evaluation block calculated from an image acquired at a timing earlier than the acquisition timing of the current image by x frames.

Since mist tends to localize, a temporal change in the brightness value, the saturation value, and the contrast value differs between the blocks (see the right graph illustrated in FIGS. 8 to 10). Since the standard deviation (see the expressions (7) to (9)) increases when mist has occurred, a change due to mist can be distinguished from a change other than a change due to mist (e.g., a change in the entire image due to a change in focus). Specifically, whether a change in evaluation value has occurred due to a change other than a change due to mist, or a local change in evaluation value has occurred due to the occurrence or the disappearance of mist can be determined by comparing the standard deviation (see the expressions (7) to (9)) with a given threshold value.

Note that the parameter is not limited to the standard deviation such as the evaluation values Vyσ[n], Vsσ[n], and Vdσ[n]. It suffices to calculate a parameter for determining whether or not a temporal change has locally occurred within all of the evaluation blocks. For example, the amount of change in the difference between the maximum value and the minimum value within all of the evaluation blocks may be calculated.

2.7. Modifications

Although the first embodiment has been described above taking an example in which the mist detection area is set to include the center area and the peripheral area of the image, the area setting method is not limited thereto. As described above, the probability that mist occurs becomes a maximum in the center area of the image when the user performs treatment using the endoscope apparatus. Therefore, only the center area (=AF area) of the image may be set to be the mist detection area, and whether or not mist has occurred may be detected by performing a determination process similar to that described above.

The probability that mist occurs is high in the center area of the image. However, mist may also occur in the peripheral area of the image. In this case, the AF evaluation value can be normally acquired until the mist that has occurred in the peripheral area of the image enters the AF area. Therefore, when only the center area of the image is set to be the mist detection area, it is possible to continue the AF control process until the mist enters the AF area.

Although the first embodiment has been described above taking an example in which the mist evaluation value is detected from the sum over the entire screen, the mist evaluation value calculation method is not limited thereto. For example, a determination process similar to that described above may be performed on each of the 3×3 blocks to detect whether or not mist has occurred, and the focus operation may be stopped when the occurrence of mist has been detected in a given number of blocks.

According to this configuration, it is possible to stop the AF control process, and fix the focus lens as soon as possible when mist has occurred at a plurality of positions within the screen. This makes it possible to prevent a situation in which an erroneous AF control process is performed.

According to the first embodiment, the mist detection section 340 detects whether or not mist has occurred from the captured image captured by the imaging device 200. Note that the captured image refers to an image processed by the pre-processing section 320. The captured image may be an image processed by the image processing section 330.

As described above with reference to FIGS. 7B to 7F, a change in image occurs when mist has occurred in an area in which treatment is performed, and diffuses over the entire captured image. Specifically, it is possible to detect the occurrence of mist from the image, and stop the AF control process by detecting such a change from the image.

More specifically, the mist detection section 340 calculates at least two (two or more) evaluation values among a first evaluation value Vy[n] based on the brightness value of the captured image, a second evaluation value Vs[n] based on the saturation value of the captured image, and a third evaluation value Vd[n] based on the contrast value of the captured image as the mist evaluation values, and detects whether or not mist has occurred based on the mist evaluation values.

In the first embodiment, the contrast value is calculated using the dynamic range. The dynamic range is the difference between the maximum value and the minimum value in the histogram of the brightness value. Note that the configuration is not limited thereto. An arbitrary index that represents the contrast of the image can be used as the third evaluation value. For example, the high-frequency component of the image may be extracted, and the third evaluation value may be calculated from the high-frequency component.

Since mist is a substance that diffuses and causes diffused reflection of illumination light, the brightness value increases, and the saturation value and the contrast value decrease (as described above with reference to FIGS. 8 to 10). Therefore, it is possible to detect whether or not mist has occurred by calculating the evaluation values from these parameters. The contrast value and the like also change due to a change in focus, for example. According to the above configuration, however, since two or more evaluation values are used in combination, it is possible to distinguish a change in parameter due to mist from a change in parameter due to a factor other than mist, and accurately detect the occurrence of mist.

As described above with reference to FIGS. 11 to 13, the mist detection section 340 calculates a temporal change in the brightness value as the first evaluation value Vy[n], calculates a temporal change in the saturation value as the second evaluation value Vs[n], and calculates a temporal change in the contrast value as the third evaluation value Vd[n].

Since the brightness value, the saturation value, and the contrast value are affected by the concentration of mist and the capturing (photographing) conditions (e.g., the type of object, the distance to the object, and the brightness of illumination light), it is difficult to set the mist detection conditions (e.g., threshold value). Therefore, it is difficult to accurately detect whether or not mist has occurred if these parameters are used directly. When a temporal change in parameter is used, the evaluation value changes when mist has occurred or disappears (change point) (see FIGS. 11 to 13), and it is possible to set conditions (e.g., maximum and minimum) that are not easily affected by the parameter value, and accurately detect whether or not mist has occurred or disappeared.

Since a temporal change in parameter occurs when mist has occurred or disappears, it is possible to determine that mist has occurred promptly after the occurrence of mist by utilizing a temporal change in parameter. It is also possible to determine that mist has disappeared when mist has disappeared sufficiently.

As described above with reference to FIGS. 11 to 13, the mist detection section 340 detects the maximum value Max{Vy} of the first evaluation value Vy[n], the minimum value Min{Vs} of the second evaluation value Vs[n], and the minimum value Min{Vd} of the third evaluation value Vd[n]. The mist detection section 340 determines that mist has occurred when the mist detection section 340 has determined that a first timing at which the maximum value Max{Vy} of the first evaluation value Vy[n] has been detected, a second timing at which the minimum value Min{Vs} of the second evaluation value Vs[n] has been detected, and a third timing at which the minimum value Min{Vd} of the third evaluation value Vd[n] has been detected, coincide with each other.

The maximum and the minimum of a temporal change in parameter occur independently of the parameter value. Therefore, when the maximum value and the minimum value of a temporal change in parameter are used as the conditions whereby it is determined that mist has occurred, the determination is not affected by the concentration of mist and the capturing conditions, and it is possible to accurately detect whether or not mist has occurred.

Note that the mist detection section 340 determines that the first timing, the second timing, and the third timing coincide with each other even when the first timing, the second timing, and the third timing differ to some extent (i.e., even when the first timing, the second timing, and the third timing do not completely coincide with each other). Specifically, since it suffices that a change in evaluation value due to mist can be distinguished from a change in evaluation value due to a factor (e.g., a change in focus) other than mist, the first timing, the second timing, and the third timing may differ by a given time required to detect the occurrence of mist. For example, the first timing, the second timing, and the third timing are measured by capturing mist, and the difference in timing that may occur statistically is set to be the given time. It is determined that the first timing, the second timing, and the third timing coincide with each other when the first timing, the second timing, and the third timing have been detected within the given time.

The mist detection section 340 may determine that mist has occurred when the first evaluation value Vy[n] is larger than a given first threshold value Thy, the second evaluation value Vs[n] is smaller than a given second threshold value Ths, and the third evaluation value Vd[n] is smaller than a given third threshold value Thd.

According to this configuration, since it is possible to determine that mist has occurred before the evaluation value reaches the maximum value or the minimum value, it is possible to more promptly detect the occurrence of mist, and stop the AF control process. This makes it possible to stop the AF control process in a state in which the amount of mist is small, and more reliably suppress a situation in which an erroneous AF control process is performed.

The focus control section 360 sets a focus evaluation value detection area (AF area) to the captured image, and calculates a focus evaluation value (AF evaluation value) for evaluating the degree of in-focus during the focus operation from the focus evaluation value detection area. The mist detection section 340 sets the mist detection area (3×3 block area) that includes the focus evaluation value detection area (see FIG. 4), and calculates the mist evaluation value for detecting whether or not mist has occurred from the image within the mist detection area.

Since an area of the image in which treatment is performed is brought into focus, the focus evaluation value detection area is set to the center area of the image in which treatment is performed (see above). Since it is most likely that mist occurs in an area of the image in which treatment is performed, it is likely that mist occurs in the focus evaluation value detection area. Therefore, it is possible to reliably detect the occurrence of mist by setting the mist detection area to include at least the focus evaluation value detection area.

More specifically, the mist detection section 340 sets a first block area (e.g., the center block among 3×3 blocks) that corresponds to the focus evaluation value detection area, and second to nth block areas situated outside the focus evaluation value detection area (e.g., eight peripheral blocks among 3×3 blocks (n is a natural number equal to or larger than 2)) to be the mist detection area. The mist detection section 340 calculates the mist evaluation values from the image within the first to nth block areas.

As described above with reference to FIGS. 7B to 7F, the abdominal cavity is filled with mist with the passing of time. Therefore, it is possible to acquire a change in image when mist (that has occurred from the mist source) spreads (diffuses) over the abdominal cavity by setting the focus evaluation value detection area (i.e., mist source) and the block areas that are situated around the focus evaluation value detection area. According to this configuration, since mist can be detected using a change specific to mist, it is possible to suppress or reduce a situation in which erroneous detection occurs due to a factor other than mist, and accurately detect the occurrence and the disappearance of mist.

According to the first embodiment, the mist detection section 340 detects whether or not mist has disappeared. The focus control section 360 resumes the focus operation that is performed during the focus control process when the mist detection section 340 has detected that mist has disappeared. Since the parameter (e.g., brightness value, saturation value, and contrast value) of the image changes when mist disappears (as described above with reference to FIGS. 7A to 10, for example), the disappearance of mist is detected by detecting a change in parameter from the image.

It is basically desirable to maintain a state in which the AF control process is performed, and an are in which treatment is performed is brought into focus. When the focus operation is resumed by detecting the disappearance of mist, it is possible to stop the AF control process only when it is impossible to implement the normal AF control process due to mist, and resume the AF control process when it has become possible to implement the normal AF control process. This makes it possible to maintain an in-focus state independently of the presence or absence of mist, and improve convenience to the user.

3. Second Embodiment

3.1. Mist Evaluation Value Calculation Method

Figure 14:
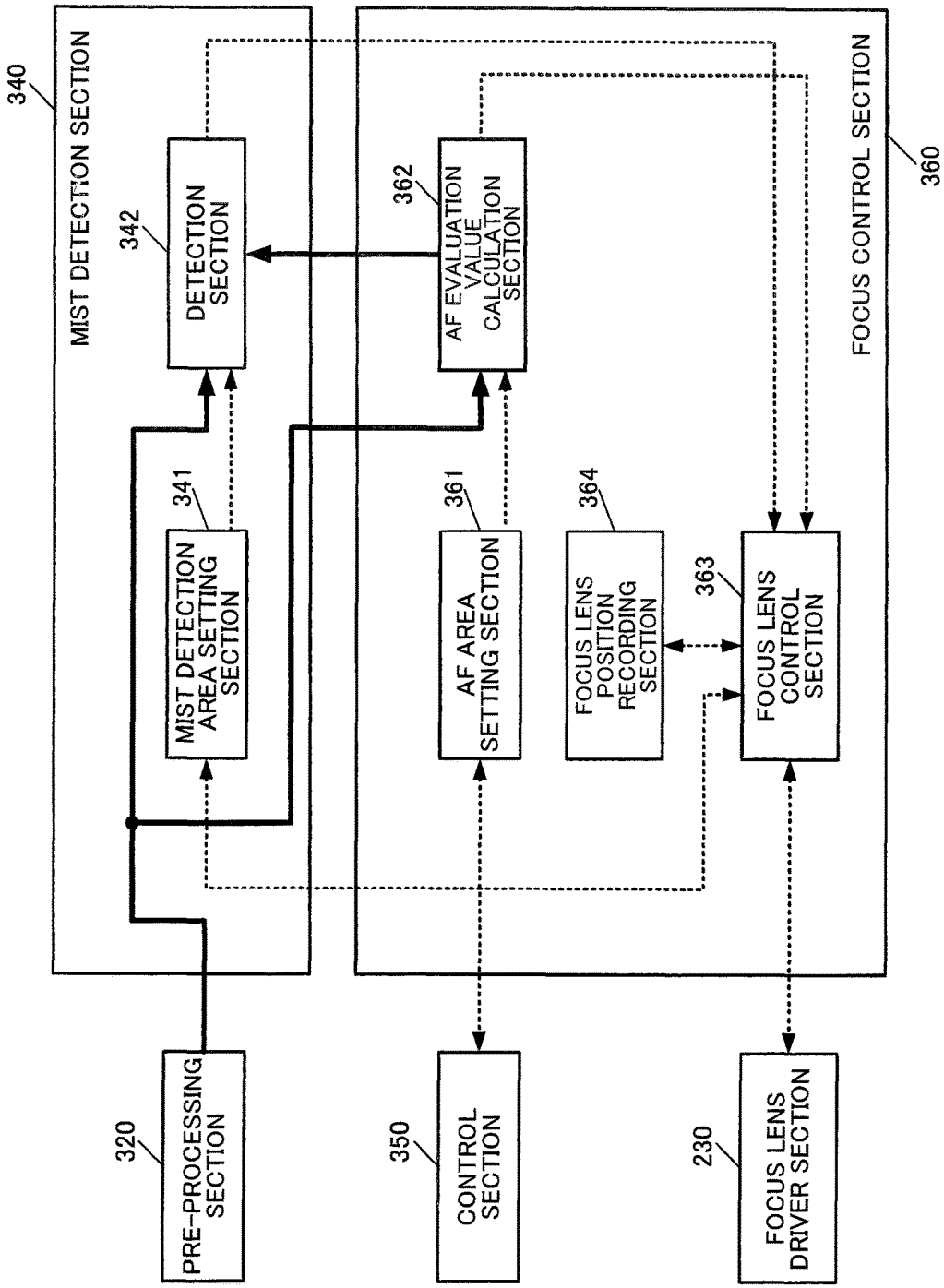
FIG. 14 illustrates a detailed configuration example of a mist detection section and a focus control section (second embodiment).

FIG. 14 illustrates a detailed configuration example of the mist detection section 340 and the focus control section 360 according to a second embodiment. Note that the endoscope apparatus is configured in the same manner as described above in connection with the first embodiment.

The mist detection section 340 includes a mist detection area setting section 341 and a detection section 342. The focus control section 360 includes an AF area setting section 361, an AF evaluation value calculation section 362, a focus lens control section 363, and a focus lens position recording section 364. Note that the same elements as those described above are indicated by the same reference signs (symbols), and description thereof is appropriately omitted.

The AF evaluation value calculation section 362 performs a band-pass filtering (BPF) process on a Y signal and a color signal, and calculates the AF evaluation value from the calculation results. The results of the band-pass filtering (BPF) process on the Y signal and the color signal are input to the detection section 342. The control section 350 controls the intensity of light (illumination light) emitted from the white light source 610 so that the image has as constant a brightness as possible. The intensity correction amount applied to the white light source 610 is input to the detection section 342.

The detection section 342 calculates the Y signal Y'[n] and the color signal C'[n] using the results of the BPF process and the intensity correction amount (see the following expressions (10) and (11)).

$$Y'[n]=(Y[n]-Bpf\{Y[n]\})/LC \quad (10)$$

$$C'[n]=(C[n]-Bpf\{C[n]\})/LC \quad (11)$$

Note that Y[n] and C[n] are signals output from the pre-processing section 320 to the detection section 342. More specifically, Y[n] is the Y signal of the image, and C[n] is the Cr signal or the Cb signal of the image. Bpf{Y[n]} and Bpf{C[n]} are signals output from the AF evaluation value calculation section 362 to the detection section 342. More specifically, Bpf{Y[n]} is the result of the BPF process on the Y signal (i.e., the Y signal within the band AfBd illustrated in FIG. 15). Bpf{C[n]} is the result of the BPF process on the color signal (i.e., the color signal within the band AfBd illustrated in FIG. 15). LC is the intensity correction amount. The higher the intensity of light, the larger the intensity correction amount LC.

Figure 15:
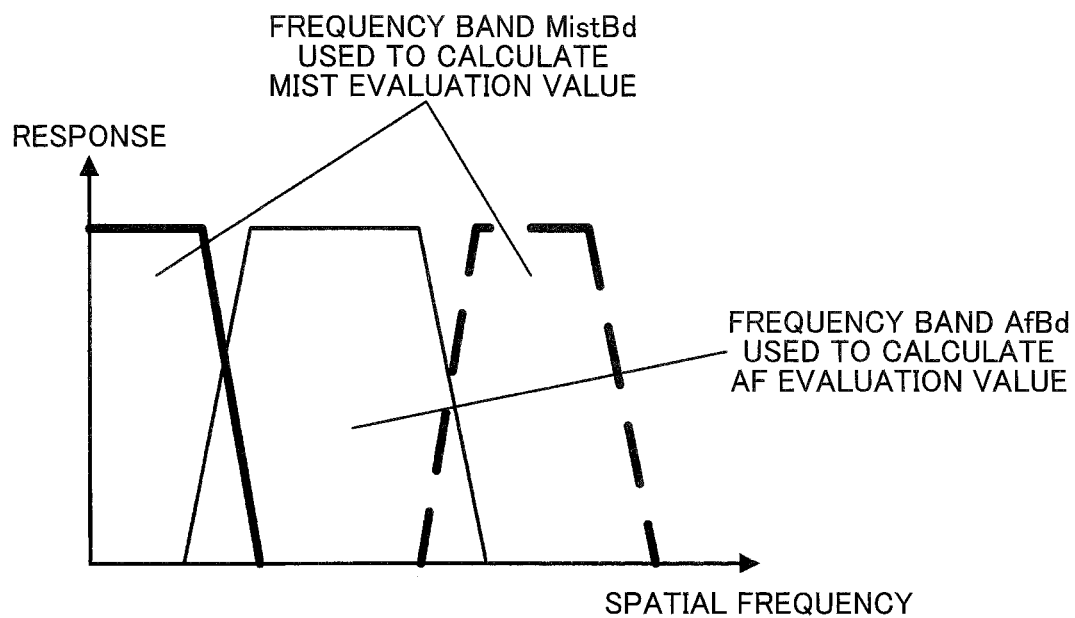
FIG. 15 is a view illustrating a spatial frequency band used for an AF evaluation value, and a spatial frequency band used for a mist evaluation value.

The Y signal Y'[n] and the color signal C'[n] are signals within the low frequency-high frequency band MistBd illustrated in FIG. 15. The detection section 342 calculates the evaluation value from these signals. Since the evaluation value is averaged corresponding to each evaluation block (or all of the evaluation blocks) (see above), the high-frequency component (see the bold dotted line illustrated in FIG. 15) within the band MistBd is substantially cut off, and only the low-frequency component (see the bold solid line) remains.

Since the evaluation value rarely changes due to a change in focus as a result of excluding the spatial frequency band used for the AF control process, it is possible to accurately detect whether or not mist has occurred while eliminating the effects of the in-focus/out-of-focus state as much as possible. Since the spatial frequency of mist is included within the low-frequency band, it is possible to accurately detect whether or not mist has occurred by calculating the evaluation value from the image signal within the low-frequency band.

Since the brightness of the image increases due to mist (as described above with reference to FIG. 8, for example), the intensity control process is performed so that the intensity of illumination light decreases. In this case, a change in evaluation value decreases, and it becomes difficult to detect whether or not mist has occurred. It is possible to cancel the effects of intensity control, and extract only a change due to mist by correcting the image signal using the intensity correction amount LC. This makes it possible to accurately detect whether or not mist has occurred.

According to the above configuration, it is possible to reduce the circuit scale as much as possible by utilizing the BPF process used to calculate the AF evaluation value. Note that a similar effect can be obtained by causing the detection section 342 to perform a low-pass filtering process.

3.2. Focus Lens Position Control Method

The focus lens position control method when stopping the focus operation is described below.

The focus lens position recording section 346 stores the focus lens positions (over a given time) determined by the focus lens control section 363. The ON/OFF information about an electrosurgical knife or an ultrasonic surgical knife is input to the focus lens control section 363 from the external interface through the control section 350.

The mist occurrence detection time n described above in connection with the first embodiment is a time at which the maximum value and the minimum value of the mist evaluation values have been reached (almost) simultaneously, or a time at which the conditions are satisfied through the threshold value determination process. In FIGS. 11 to 13, the occurrence of mist is detected at the time tC or a time between the times tB and tC. Therefore, the mist occurrence detection time is not a time immediately after the occurrence of mist (i.e., is delayed to some extent with respect to the mist occurrence time).

In the second embodiment, the focus lens positions over a given time are recorded in order to compensate for the delay. The delay compensation time is a time that precedes the mist occurrence detection time n and ends when the mist evaluation value has become smaller than a given threshold value. For example, a temporal change in mist is captured, and calculated statistically. The focus lens control section 363 moves (returns) the focus lens to the focus lens position at a time that precedes the mist occurrence detection time n by the given time when the occurrence of mist has been detected, and the focus operation is stopped.

According to this configuration, since the actual mist occurrence time can be determined more accurately, the focus operation can be stopped at the focus lens position at the actual mist occurrence time. Specifically, even when an erroneous AF control process is performed, and the object has become out of focus during a period from the occurrence of mist to the timing at which the occurrence of mist is detected by the mist detection section 340, it is possible to return the focus lens to the in-focus position at a timing immediately before mist occurs.

Moreover, it is possible to improve the accuracy of the delay compensation time by utilizing the ON/OFF information about an electrosurgical knife or an ultrasonic surgical knife input from the external interface through the control section 350. Specifically, the focus lens control section 363 reads the focus lens position at a time that precedes the mist occurrence detection time n at which an electrosurgical knife or an ultrasonic surgical knife has been most recently set to an ON state from the focus lens position recording section 364. The focus lens control section 363 moves the focus lens to the focus lens position read from the focus lens position recording section 364 when the occurrence of mist has been detected, and the focus operation is stopped.

When a time at which an electrosurgical knife or an ultrasonic surgical knife has been set to an ON state is used as the mist occurrence time, it is impossible to detect the mist disappearance time when mist has not occurred, and determine the time at which the AF control process is to be resumed. This problem can be solved by performing the process that detects whether or not mist has occurred from the image (see the first embodiment) after an electrosurgical knife or an ultrasonic surgical knife has been set to an ON state.

According to the second embodiment, the focus control section 360 calculates the focus evaluation value (AF evaluation value) for evaluating the degree of in-focus during the focus operation based on the component of the captured image within a specific frequency band (band AfBd illustrated in FIG. 15). The mist detection section 340 calculates the mist evaluation value for detecting whether or not mist has occurred based on the component within a frequency band (low-frequency band included in the band MistBd) that is lower than the specific frequency band.

Since the spatial frequency of mist is included within the low-frequency band, it is possible to efficiently detect a change due to mist by calculating the mist evaluation value from the image within the low-frequency band. It is considered that the band from which the focus evaluation value is calculated is most easily affected when a change in focus has occurred due to the AF operation, for example. However, it is possible to accurately detect whether or not mist has occurred or disappeared without being affected by a change in focus by calculating the mist evaluation value from the image within a band lower than the band from which the focus evaluation value is calculated.

According to the second embodiment, the endoscope apparatus includes a light intensity control section (control section 350) that controls the intensity of illumination light that is applied to the object that is captured by the imaging device 200. The mist detection section 340 corrects the pixel value of the captured image based on the intensity of illumination light (see the expressions (10) and (11)), and calculates the mist evaluation value for detecting whether or not mist has occurred based on the corrected pixel value.

When the intensity of illumination light has changed, the parameter (e.g., brightness value) changes, and it may be difficult to accurately detect whether or not mist has occurred or disappeared. Since a change in parameter due to mist can be extracted by correcting the pixel value using the intensity (intensity correction amount LC) of illumination light, it is possible to improve the mist detection accuracy.

According to the second embodiment, the focus control section 360 moves the focus lens to the focus lens position at a timing that precedes the timing at which the mist detection section 340 has detected that mist has occurred by a given time when stopping the focus operation that is performed during the focus control process.

Since it is likely that mist occurs in the AF area (see above), the AF control process may be affected by mist immediately after mist has occurred. Therefore, an erroneous AF control process may have been performed at a timing at which the occurrence of mist has been detected. However, when the previous focus lens positions are stored, and the focus lens is moved to the focus lens position at a timing that precedes the timing at which the occurrence of mist has been detected by a given time, it is possible to stop the focus operation at the focus lens position before the occurrence of mist (or immediately after the occurrence of mist) at which it is not likely that an erroneous AF control process is performed.

The mist is mist that occurs from the object when treatment using a treatment tool (e.g., electrosurgical knife or ultrasonic surgical knife) is performed. The focus control section 360 moves the focus lens to the focus lens position at a timing at which the treatment tool has been set to an ON state when stopping the focus operation that is performed during the focus control process.

When using a treatment tool that requires the supply of power, treatment is performed after the treatment tool has been set to an ON state, and mist occurs at least after the treatment tool has been set to an ON state. Specifically, mist has not occurred when the treatment tool has been set to an ON state. Therefore, it is possible to stop the AF control process in a state in which an area in which the treatment is performed is reliably brought into focus by setting the focus lens to the focus lens position when the treatment tool has been set to an ON state.

The embodiments to which the invention is applied and the modifications thereof have been described above. Note that the invention is not limited to the above embodiments and the modifications thereof. Various modifications and variations may be made without departing from the scope of the invention. A plurality of elements described above in connection with the embodiments and the modifications thereof may be appropriately combined to implement various configurations. For example, some elements may be omitted from the elements described above in connection with the embodiments and the modifications thereof. Some of the elements described above in connection with different embodiments or modifications may be appropriately combined. Specifically, various modifications and applications are possible without materially departing from the novel teachings and advantages of the invention. Any term cited with a different term having a broader meaning or the same meaning at least once in the specification and the drawings can be replaced by the different term in any place in the specification and the drawings.

What is claimed is:

1. An endoscope apparatus comprising:
a processor comprising hardware, wherein the processor is configured to:
start performing a focus operation process comprising controlling a position of a focus lens included in an optical system that is included in an imaging device;
perform a mist detection process that detects, from a captured image captured by the imaging device, whether or not mist that occurs from an object when treatment using a treatment tool is performed within the field of view of the imaging device has occurred; and
stop the focus operation process in response to the mist detection process detecting that the mist has occurred,
wherein the mist detection process performed by the processor comprises:
calculating at least two evaluation values among:
a first evaluation value that is a temporal change in a brightness value of the captured image;
a second evaluation value that is a temporal change in a saturation value of the captured image; and
a third evaluation value that is a temporal change in a contrast value of the captured image,
as mist evaluation values; and
detecting whether or not the mist has occurred based on the mist evaluation values.

2. The endoscope apparatus according to claim 1,
wherein the mist detection process performed by the processor comprises:
detecting:
a maximum value of the first evaluation value;
a minimum value of the second evaluation value; and
a minimum value of the third evaluation value; and
determining that the mist has occurred in response to determining that a first timing at which the maximum value of the first evaluation value has been detected, a second timing at which the minimum value of the second evaluation value has been detected, and a third timing at which the minimum value of the third evaluation value has been detected, coincide with each other.

3. The endoscope apparatus according to claim 1,
wherein the mist detection process performed by the processor comprises determining that the mist has occurred in response to determining that the first evaluation value is larger than a given first threshold value, the second evaluation value is smaller than a given second threshold value, and the third evaluation value is smaller than a given third threshold value.

4. The endoscope apparatus according to claim 1,
wherein the focus operation process performed by the processor comprises calculating a focus evaluation value for evaluating a degree of in-focus during the focus operation based on a component of the captured image within a specific frequency band, and
wherein the mist detection process performed by the processor comprises calculating a mist evaluation value for detecting whether or not the mist has occurred based on a component within a frequency band that is lower than the specific frequency band.

5. The endoscope apparatus according to claim 1,
wherein the processor is configured to perform a light intensity control process comprising controlling intensity of illumination light that is applied to an object that is captured in the captured image by the imaging device, and
wherein the mist detection process performed by processor comprises:
correcting a pixel value of the captured image based on the intensity of the illumination light; and
calculating a mist evaluation value for detecting whether or not the mist has occurred based on the corrected pixel value.

6. The endoscope apparatus according to claim 1,
wherein the focus operation process performed by the processor comprises:
setting a focus evaluation value detection area to the captured image; image, and
calculating a focus evaluation value for evaluating a degree of in-focus during the focus operation process from the focus evaluation value detection area, and
wherein the mist detection process performed by the processor comprises:
setting a mist detection area that includes the focus evaluation value detection area; and
calculating a mist evaluation value for detecting whether or not the mist has occurred from an image within the mist detection area.

7. The endoscope apparatus according to claim 6,
wherein the focus operation process performed by the processor comprises:
setting a first block area that corresponds to the focus evaluation value detection area, and second to nth block areas (n is a natural number equal to or larger than 2) situated outside the focus evaluation value detection area to be the mist detection area; and
calculating the mist evaluation value from an image within the first to nth block areas.

8. The endoscope apparatus according to claim 1,
wherein the mist detection process performed by the processor comprises:
setting a plurality of block areas to the captured image to be a mist detection area;
calculating an average brightness value, an average saturation value, and an average contrast value corresponding to each of the plurality of block area; and
determining whether or not the mist has occurred based on the average brightness value, the average saturation value, and the average contrast value.

9. The endoscope apparatus according to claim 8,
wherein the mist detection process performed by the processor comprises:
adding up the average brightness values of the plurality of block areas to calculate a first evaluation value;
adding up the average saturation values of the plurality of block areas to calculate a second evaluation value;
adding up the average contrast values of the plurality of block areas to calculate a third evaluation value; and
detecting whether or not the mist has occurred based on the first evaluation value, the second evaluation value, and the third evaluation value.

10. The endoscope apparatus according to claim 8,
wherein the mist detection process performed by the processor comprises:
calculating:
a maximum value among the average brightness values of the plurality of block areas to be a first evaluation value;

a maximum value among the average saturation values of the plurality of block areas to be a second evaluation value; and
a maximum value among the average contrast values of the plurality of block areas to be a third evaluation value; and
detecting whether or not the mist has occurred based on the first evaluation value, the second evaluation value, and the third evaluation value.

11. The endoscope apparatus according to claim 8, wherein the mist detection process performed by the processor comprises:
calculating:
a standard deviation of the average brightness values of the plurality of block areas to be a first evaluation value;
a standard deviation of the average saturation values of the plurality of block areas to be a second evaluation value; and
a standard deviation of the average contrast values of the plurality of block areas to be a third evaluation value; and
detecting whether or not the mist has occurred based on the first evaluation value, the second evaluation value, and the third evaluation value.

12. The endoscope apparatus according to claim 1, wherein the processor is configured to:
determine whether or not the mist that was determined to have occurred has disappeared; and
resume the focus operation process that was stopped in response to determining that the mist has disappeared.

13. The endoscope apparatus according to claim 12, wherein the processor is configured to:
calculate at least two evaluation values among a first evaluation value, a second evaluation value, and a third evaluation value as mist evaluation values, and
determine whether or not the mist has disappeared based on the at least two evaluation values,
wherein the first evaluation value is a temporal change in a brightness value of another captured image captured by the imaging device,
wherein the second evaluation value is a temporal change in a saturation value of the another captured image, and
wherein the third evaluation value is a temporal change in a contrast value of the another captured image.

14. The endoscope apparatus according to claim 1, wherein stopping the focus operation process performed by the processor comprises moving the focus lens to a position of the focus lens at a timing that precedes a timing at which the processor, performing the mist detection process, detects that the mist has occurred by a given time.

15. The endoscope apparatus according to claim 1, wherein the mist detection process performed by the processor comprises detecting whether or not the mist has occurred based on whether or not the treatment tool has been set to an ON state.

16. The endoscope apparatus according to claim 1, wherein stopping the focus operation process performed the processor comprises moving the focus lens to a position of the focus lens at a timing at which the treatment tool has been set to an ON state.

17. The endoscope apparatus according to claim 15, wherein stopping the focus operation process performed by the processor comprises moving the focus lens to a position of the focus lens at a timing at which the treatment tool has been set to the ON state.

18. A method for operating an endoscope apparatus comprising:
starting to perform a focus operation process comprising controlling a position of a focus lens included in an optical system that is included in an imaging device;
performing a mist detection process comprising detecting, from a captured image captured by the imaging device, whether or not mist that occurs from an object when treatment using a treatment tool is performed within the field of view of the imaging device has occurred; and
stopping the focus operation process in response to the mist detection process detecting that the mist has occurred,
wherein the mist detection process comprises:
calculating at least two evaluation values among:
a first evaluation value that is a temporal change in a brightness value of the captured image;
a second evaluation value that is a temporal change in a saturation value of the captured image; and
a third evaluation value that is a temporal change in a contrast value of the captured image,
as mist evaluation values; and
detecting whether or not the mist has occurred based on the mist evaluation values.

19. A non-transitory computer-readable storage medium device storing instructions for operating an endoscope apparatus, wherein the instructions cause a computer to at least:
start to perform a focus operation process comprising controlling a position of a focus lens included in an optical system that is included in an imaging device;
perform a mist detection process comprising detecting, from a captured image captured by the imaging device, whether or not mist that occurs from an object when treatment using a treatment tool is performed within the field of view of the imaging device has occurred; and
stopping the focus operation process in response to the mist detection process detecting that the mist has occurred,
wherein the mist detection process comprises:
calculating at least two evaluation values among:
a first evaluation value that is a temporal change in a brightness value of the captured image;
a second evaluation value that is a temporal change in a saturation value of the captured image; and
a third evaluation value that is a temporal change in a contrast value of the captured image,
as mist evaluation values; and
detecting whether or not the mist has occurred based on the mist evaluation values.

* * * * *